US008623886B2

(12) United States Patent
Wilson (10) Patent No.: US 8,623,886 B2
(45) Date of Patent: Jan. 7, 2014

(54) PHYCOTOXINS AND USES THEREOF (75) Inventor: Nestor Antonio Lagos Wilson, Santiago (CL)

(73) Assignee: Phytotox Limited, Hamilton (BM)

( * ) Notice: Subject to any disclaimer, the term of this patent is extended or adjusted under 35 U.S.C. 154(b) by 26 days.

(21) Appl. No.: 13/526,868

(22) Filed: Jun. 19, 2012

(65) Prior Publication Data

US 2012/0322818 A1 Dec. 20, 2012

Related U.S. Application Data

(63) Continuation of application No. 11/568,752, filed as application No. PCT/US2005/015946 on May 6, 2005, now abandoned.

(60) Provisional application No. 60/569,383, filed on May 7, 2004, provisional application No. 60/569,380, filed on May 7, 2004.

(51) Int. Cl.
*A61K 31/505* (2006.01)

(52) U.S. Cl.
USPC .......................................................... 514/268

(58) Field of Classification Search
USPC .......................................................... 514/268
See application file for complete search history.

(56) References Cited

U.S. PATENT DOCUMENTS

| | | | | |
|---|---|---|---|---|
| 6,447,787 | B1 * | 9/2002 | Gassner et al. | 424/247.1 |
| 2004/0009180 | A1 * | 1/2004 | Donovan | 424/184.1 |

OTHER PUBLICATIONS

Patockaa (A Brief Review of Natural Nonprotein Neurotoxins, Applied Science and Analysis Newsletter, ISSN 1057-9419, 2002).*

Lin (Paralytic toxins in Taiwanese Starfish, Toxicon, vol. 36, No. 5, pp. 799-803, 1998).*

Schantz et al., "Properties and Use of Botulinum Toxin and Other Microbial Neruotoxins in Medicine," Microbiological Review. Mar. 1992, p. 80-99.

Llewelyn, Saxtoxin, a toxic marine natural product that targets a multitude of receptors, Nat. Prod. Rep., 2006, 23 , 200-222.

* cited by examiner

*Primary Examiner* — Frederick Krass
*Assistant Examiner* — Adam C Milligan
(74) *Attorney, Agent, or Firm* — Clark G. Sullivan; Troutman Sanders LLP

(57) ABSTRACT

Pharmaceutical compositions for interfering with neuronal transmission comprising an effective amount of at least one tricyclic 3,4-propinoperhydropurine and at least one additional compound are disclosed. Preparations for topical applications are provided that comprise an effective amount of the composition of the invention and a pharmacologically acceptable carrier. Methods of interfering with neuronal transmission comprising topical application of an effective amount of the at least one tricyclic 3,4-propinoperhydropurine are provided for treatment of a variety of indications that relate to muscle relaxation, anesthesia, muscle spasms and similar causes.

10 Claims, 4 Drawing Sheets

Figure 1: GTX injection points for fibromyalgia patients

Figure 2: GTX injection points for tensional cephalea (tension headache) patients CEFALEA TENSIONAL: Puntos Gatillo e Infiltrados Figure 3A. Patient with blepharospasm, before toxin application Figure 3B. Patient with blepharospasm, 1 minutes after toxin application Figure 4A. Patient with permanent hemifacial spasm before toxin application Figure 4B. Patient with permanent hemifacial spasm after toxin application

PHYCOTOXINS AND USES THEREOF

RELATED APPLICATIONS

This application is a continuation of U.S. Ser. No. 11/568,752, filed Nov. 6, 2006 now abandoned, which is a national stage application of PCT/US05/15946, filed May 6, 2005, which claims priority to U.S. Provisional Application Nos. 60/569,383 and 60/569,380, both filed May 7, 2004.

FIELD OF THE INVENTION

This invention relates to methods of treating muscle disorders and to pharmaceutical compositions containing heterocyclic guanidine-type compounds which can be used in the methods, as well as for other purposes.

BACKGROUND OF THE INVENTION

Paralytic shellfish poisoning (PSP) results from a mixture of phycotoxins that bind reversibly to a receptor site on the voltage-gated sodium channel found in excitable cells. The primary clinical symptom is an acute paralytic illness. Phycotoxins or algal toxins are produced by microscopic planktonic algae. These toxins accumulate on filter feeders such as bivalves. Consumption of phycotoxin-contaminated shellfish results in six diseases in humans: PSP, amnesic shellfish poisoning (ASP), Diarrheic shellfish poisoning (DSP), neurotoxic shellfish poisoning (NSP), ciguatera poisoning (CP), and cyanobacterial poisoning (CNP).

The phycotoxins that produce PSP have a common structure of 3,4,6-trialquil tetrahydropurine. Twenty-six naturally occurring PSP have been described. These phycotoxins are non-protein, low molecular weight compounds of between 289 and 450 daltons.

The gonyautoxins (GTXs) are the most abundant PSP toxins found in shellfish extract accounting for over 80% of the total toxin content. The high toxicity of the PSP toxins is due to the reversible binding to a receptor site on the voltage-gated sodium channel on excitable cells, thus blocking the influx of sodium ions and preventing nerve and muscle cells from producing action potentials, thereby blocking neuronal transmission and causing death in mammals via respiratory arrest and cardiovascular shock. Application of small amounts of PSP toxin produces a flaccid paralysis of striated muscle for periods that are dose dependant.

The gonyautoxins of the present invention provide a local anesthetic for use in mammals either by injecting a liquid preparation or as a topical anesthetic applied to the skin of mammal.

The gonyautoxins of the present invention also provide surprising beneficial results in the treatment of a variety of ailments, which may be caused or aggravated by muscle disorders, muscle spasms or muscle action.

There remains a need for a fast acting and long lasting topical anesthetic which does not damage the skin or result in rashes, irritations, sensitization or other discomforts. There also remains a need for more effective, less invasive treatments for a variety of ailments.

SUMMARY OF THE INVENTION

In a first aspect of the invention, methods of treating various ailments comprising the step of administering an effective amount of the pharmaceutical compositions containing one or more gonyautoxins, are provided. In the methods, muscle relaxation and/or anesthetization is employed for the purpose of providing a beneficial treatment of a variety of ailments which may related to muscle disorders, muscle spasms, or may be caused or aggravated by muscle action.

In another aspect of the invention, pharmaceutical compositions for interfering with neuronal transmission comprising an effective amount of at least one tricyclic 3,4 propinoperhydropurine and at least one other active ingredient are provided.

In another aspect of the invention, preparations for facial rejuvenation are provided that comprise an effective amount of the composition of the invention and a facial cream.

DETAILED DESCRIPTION OF THE INVENTION

The following definitions apply to the description of the invention.

As used herein, "an effective amount" is that amount sufficient to interfere with neuronal transmission by blocking at least some of the presynaptic release of the neurotransmitter acetylcholine in the neuromuscular plate, thus interfering with transmission, paralyzing the muscle and preventing it from contracting, or producing a relaxation of contracted muscles.

Amounts are given in units of activity. One unit of activity corresponds to an amount of the composition of the invention necessary to block the muscular contractions of the crural biceps of a 20 gram CF1 albino or a BALB-C strain mouse leg for 1.5 to 2.0 hours. The toxin is intramuscularly injected in the crural biceps of the mouse right leg in a volume of 0.5 ml. The left leg is used as a control.

In order to measure the amount of toxin used in each dose, High Performance Liquid Chromatography (HPLC) analysis can be performed with on line fluorescence detection (HPLC-FLD). This method allows the measurement of the mass of each toxin in any mixture, extract or pharmaceutical formulation.

It must be noted that, as used in this specification and the appended claims, the singular forms "a," "an" and "the" include plural referents unless the context clearly dictates otherwise. Thus, for example, reference to "a pharmacologically active agent" includes a mixture of two or more active agents, reference to "an enhancer" includes mixtures of two or more enhancers, and the like.

In describing and claiming the present invention, the following terminology will be used in accordance with the definitions set out below.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. The present method of "treating" a mammal, as the term is used herein, thus encompasses both prevention of a disorder in a predisposed individual and treatment of the disorder in a clinically symptomatic individual.

The terms "active agent," "drug" and "pharmacologically active agent" are used interchangeably herein to refer to a chemical material or compound that induces a desired effect, and include agents that are therapeutically effective, prophylactically effective, or cosmetically effective. Also included are derivatives and analogs of those compounds or classes of compounds specifically mentioned which also induce the desired effect.

"By therapeutically effective" amount is meant a nontoxic but sufficient amount of an active agent to provide the desired therapeutic effect.

By "transdermal" drug delivery is meant administration of a drug to the skin surface of an individual so that the drug passes through the skin tissue and into the individual's blood stream, thereby producing a systemic effect. The term "transdermal" is intended to include "transmucosal" drug administration, i.e., administration of a drug to the mucosal (e.g., sublingual, buccal, vaginal, rectal) surface of an individual so that the drug passes through the mucosal tissue and into the individual's blood stream.

The term "topical administration" is used in its conventional sense to mean delivery of a topical drug of a pharmacologically active agent to the skin or mucosa, as in, for example, the treatment of various skin disorders. Topical drug administration, in contrast to transdermal administration, provides a local rather than a systemic effect. Unless otherwise stated or implied, the teams "topical drug administration" and "transdermal drug administration" are used interchangeably.

The term "body surface" is used to refer to skin or mucosal tissue.

By "predetermined area" of skin or mucosal tissue, which refers to the area of skin or mucosal tissue through which an active agent is delivered, and is intended to define an area of intact unbroken living skin or mucosal tissue. That area will usually be in the range of about 5 $cm^2$ to about 200 $cm^2$, more usually in the range of about 5 $cm^2$ to about 100 $cm^2$, preferably in the range of about 20 $cm^2$ to about 60 $cm^2$. However, it will be appreciated by those skilled in the art of drug delivery that the area of skin or mucosal tissue through which the drug is administered may vary significantly, depending on factors such as the desired treatment, whether a delivery device is used, dose, and the size of the treatment area, and other factors.

"Penetration enhancement" or "permeation enhancement" as used herein refers to an increase in the rate at which the active agent permeates through the skin or mucosal membrane, relative to penetration of the same active agent when applied alone (i.e., the "flux" of the agent through the body surface). The enhanced permeation effected through the use of such enhancers can be observed by measuring the rate of diffusion of drug through animal or human skin using, for example, a Franz diffusion apparatus as known in the art.

An "effective amount of a permeation enhancer" refers to a non-toxic amount or quantity of the enhancer or penetration-enhancing treatment, which is sufficient to provide the desired increase in penetration rate. Permeation enhancers may also influence the depth of penetration, rate of administration, and amount of drug delivered.

"Carriers" or "vehicles" as used herein refer to carrier materials suitable for transdermal or topical drug administration. Carriers and vehicles useful herein include any such materials known in the art which is non-toxic in the amounts used, and does not interact with other components of the composition in a deleterious manner.

The term "aqueous" refers to a formulation or drug delivery system that contains water or that becomes water-containing following application to the skin or mucosal tissue.

It has been surprisingly found that certain methods of the present invention not only provide practically immediate anesthetic and muscle relaxant effects, but also provide beneficial muscle relaxation effects over an unexpectedly long period. As a result, certain methods of the present invention are particularly well-suited to treatment of neuromuscular disorders associated with spastic muscles, sympathetic neuronal disorders such as hyper active sweat glands, to reduce inflammation or pain due to inflammation, to treat blepharospasm, anal fissure and achalasia, strabismus, focal dystonia, hyperhydrosis, urologic disorders by, for example, urinary bladder relaxation, muscular spasm-related pain management, muscular spasms, wound treatment including wound suturing and stapling, shave biopsy, facial wrinkle reduction or removal, carpal-tunnel syndrome, fibromyalgia, joint flare, joint pain, post-operative pain management, arthritis, sciatica, tendonitis, neck pain or neck injury, back pain, hemifacial spasm, hyperfunctional larynx, juvenile cerebral palsy, spasticity, headaches including migraine headaches, writers cramp, miofacial pain, tremors, tics, bruxism, temporomandibular joint pain, cervical dystonia, oramandibular dystonia, dental anesthesia, treatment of dental pain, hair growth, gastrointestinal disorders, hyperfunctional facial lines, cosmetic disorders, shoulder pain, rotator cuff injuries, peripheral nerve dysfunction, migraine or tension headaches, disorders of the upper and lower esophageal sphincter, gastroparesis, hypertrophic pyloric stenosis, hemorrhoids, proctalgia fugax, irritable bowel syndrome, muscular spasms, vasospastic disorders, disorders involving uterine, or bladder spasm, sphincter of Oddi dysfunction, and short-segment Hirschprung's, strokes and problems with motor control as well as reducing or eliminating the pain associated with injections (painful injections), and I.V. needle insertions. The unexpected longer term muscle relaxation effects of the GTX compounds have been found to facilitate the healing process.

The phycotoxins employed in the methods and compositions of the present invention are non-protein, low molecular weight compounds of between 289 and 450 daltons. This provides several advantages over prior art compositions used for similar purposes. First, since the phycotoxins are non-protein, the likelihood of allergic reactions to the phycotoxins is very low. Second, the small size of the phycotoxins makes them excellent candidates for transdermal delivery. Also, the phycotoxins of the present invention are very potent, relative to, for example, Botulin A toxin, and thus smaller amounts can be used to achieve longer lasting effects. In addition, the phycotoxins of the present invention often realize their effects in a shorter time period, in comparison to Botulin A toxin. Also, the small size of the phycotoxins allows them to be passed out of the body relatively quickly, thereby reducing the risk of harmful side effects or toxin buildup in the body.

The compositions used in the methods of the present invention comprise an effective amount of at least one phycotoxin. More preferably, the compositions of the invention comprise an effective amount of at least one compound represented by formula I set forth below:

Formula I wherein $R_1$ and $R_5$ are independently selected from the group consisting of —H and —OH; $R_2$ and $R_3$ are independently selected from the group consisting of —H and —$SO_3^-$; and $R_4$ is selected from the group consisting of H, —OH, —$COONH_2$, —$COONHSO_3^-$ and —$COOCH_3$, with the proviso that either one of $R_2$ and $R_3$ must be —$OSO_3^-$, or $R_4$ must be —$COONHSO_3^-$, and a pharmacologically acceptable topical carrier.

Preferred tricyclic 3,4-propinoperhydropurines in accordance with the present invention are the gonyautoxins (hereinafter "GTX") of the formula I as set forth in the table below.

more than 32 units of activity up to a maximum of about 5000 units of activity of phycotoxins. Even more preferably, each dose includes more than 32 to about 1000 units of activity of phycotoxins, more preferably, from more than 40 to 15 about 1000 units of activity of phycotoxins, and even more preferably, from about 50 to about 500 units of activity of phycotoxins. Most preferably, each dose includes about 75 to about 200 units of activity of phycotoxins. Doses may be repeated from time-to-time, as needed, to continue muscle relaxation until the desired effect is obtained.

According one method of the present invention, animals or humans are treated by direct, local injection of a composition of the invention into a muscle or in the vicinity of a muscle. In some embodiments, the muscle at the location of injection exhibits elevated tone or spasms, though this is not necessary for the effectiveness of all treatments. Each injection may be limited to not more than two milliliters of composition, including solvents, adjuvants and/or carrier materials. Administration may be accomplished, for example, using a one milliliter, tuberculin-type disposable syringe with a twenty-seven to thirty gauge needle. Alternatively, for certain methods, it may be desirable to administer the dosage using an endoscope such as that described in U.S. Pat. No. 5,674,205, the disclosure of which is hereby incorporated by reference for the purpose of providing details of an endoscope suitable for use in the method of the present invention. In one embodiment, an injectable solution of a mixture of GTX 2 and GTX 3, optionally containing one or both of GTX 1 and GTX 4, in 0.9% sodium chloride solution is employed. The injectable solution may have any suitable concentration but preferably contains more than 40 up to about 1000 units per milliliter. In one embodiment, the ratio of GTX 2 to GTX 3 in the injectable solution is about 2:1.

Alternatively, the pharmaceutical compositions of the invention may be applied locally in the form of a topical preparation. To form a topical preparation, an effective

TABLE 1

| GTX Compounds | | | | | |
|---|---|---|---|---|---|
| Compound | $R_1$ | $R_2$ | $R_3$ | $R_4$ | $R_5$ |
| Gonyautoxin 1 | —OH | —H | —$OSO_3^-$ | —$COONH_2$ | —OH |
| Gonyautoxin 2 | —H | —H | —$OSO_3^-$ | —$COONH_2$ | —OH |
| Gonyautoxin 3 | —H | —$OSO_3^-$ | —H | —$COONH_2$ | —OH |
| Gonyautoxin 4 | —OH | —$OSO_3^-$ | —H | —$COONH_2$ | —OH |
| Gonyautoxin 5 | —H | —H | —H | —$COONHSO_3^-$ | —OH |

The methods and formulations of the invention can be administered by injection, topical or transdermal administration of phycotoxin to treat any condition, disease or disorder that is responsive to administration of phycotoxin. Typically, the formulations and delivery systems of the invention are used to administer a phycotoxin as an anesthetic agent (i.e., for pain relief), to relax muscles and/or decrease muscle contractions. Most commonly, the compounds are used as a muscle relaxant or to decrease muscle contractions.

Each dose may include from 1 to about 5000 units of activity of phycotoxins. More preferably, each dose includes amount of the pharmaceutical composition of the invention is added to a pharmacologically acceptable topical carrier. The composition, when applied topically, may be in any form suitable for application to the body surface, and may comprise, for example, a cream, lotion, solution, gel, ointment, paste or the like, and/or may be prepared so as to contain liposomes, micelles, and/or microspheres. The topical preparation may include from about 0.0001% to about 0.01% by weight of the GTX compounds, based on the weight of the preparation. Alternatively, the topical preparation may include from about 0.001% to about 0.01% by weight of the GTX compounds, based on the weight of the preparation.

In the methods of the invention, the pharmaceutical composition may be directly applied to the body surface or may involve use of a drug delivery device. Thus, a formulation or drug reservoir may be aqueous, i.e., contain water, or may be nonaqueous and used in combination with an occlusive overlayer so that moisture evaporating from the body surface is maintained within the formulation or transdermal system during drug administration. In some cases, however, e.g., with an occlusive gel, a non-aqueous formulation may be used with or without an occlusive layer.

It has been found, for example, that in pain relief applications such as treatment of tension headache and fibromyalgia, an administration of one dose provides effects that last for at least four weeks and sometimes significantly longer. It was not expected that administration of GTX toxins could provide such long periods of relief In addition, it has been found that the administration of GTX toxins can treat indications that are resistant to other toxins, such as Botulinum A toxin. This is also an unexpected advantage of the GTX toxins.

It will be understood by those skilled in the art that in the methods of the present invention, the phycotoxin, or combination of phycotoxins may be administered with or without additional compound(s), and, if administered with additional compound(s), the phycotoxins may be administered, before, during or after the administration of the additional compound(s). Additionally the administration means for the phycotoxin and additional compound(s) may also be different, for example, the phycotoxin may be administered by transdermal application prior to administration of a painful injection.

Another aspect of the invention relates to compositions comprising certain phycotoxins, in combination with at least one other compound. Such compositions are suitable for a variety of applications and can, for example, be used for many cosmetic and clinical applications to potentially avoid surgery, potentially reduce side effects, and to minimize allergies, immune rejection or hematoma. It has also been found that certain phycotoxins can be used in cosmetic and therapeutic methods with advantageous results, particularly when muscle disorders, muscle spasms or muscle action is a cause or contributing factor to the condition at issue.

The compositions of the invention comprise an effective amount of at least one phycotoxin. More preferably, the compositions of the invention comprise an effective amount of at least one compound represented by formula I set forth below:

Formula I wherein $R_1$ and $R_5$ are independently selected from the group consisting of —H and —OH; $R_2$ and $R_3$ are independently selected from the group consisting of —H and —$SO_3$; and $R_4$ is selected from the group consisting of H, —OH, —$COONH_2$, —$COONHSO_3$ and —$COOCH_3$, with the proviso that either one of $R_2$ and $R_3$ must be —$OSO_3$, or $R_4$ must be —$COONHSO_3$, and a pharmacologically acceptable topical carrier.

Preferred tricyclic 3,4-propinoperhydropurines in accordance with the present invention are the gonyautoxins (hereinafter "GTX") of the formula I as set forth in the table below.

TABLE 1

| GTX Compounds | | | | | |
|---|---|---|---|---|---|
| Compound | $R_1$ | $R_2$ | $R_3$ | $R_4$ | $R_5$ |
| Gonyautoxin 1 | —OH | —H | —$OSO^-_3$ | —$COONH_2$ | —OH |
| Gonyautoxin 2 | —H | —H | —$OSO^-_3$ | —$COONH_2$ | —OH |
| Gonyautoxin 3 | —H | —$OSO^-_3$ | —H | —$COONH_2$ | —OH |
| Gonyautoxin 4 | —OH | —$OSO^-_3$ | —H | —$COONH_2$ | —OH |
| Gonyautoxin 5 | —H | —H | —H | —$COONHSO^-_3$ | —OH |

In one aspect of the invention, the pharmaceutical compositions comprise at least one phycotoxin in combination with at least one additional compound. In a more preferred aspect, the compositions of the present invention include at least one GTX compound selected from GTX 1, GTX 2, GTX 3, GTX 4 and GTX 5, at least one local anesthetic selected from betacaine-LA, tetracaine, mepivacaine, prilocalne, etidocaine, bupivacaine, lidocaine, morphine, TAC (tetracaine, adrenaline (epinephrine) and cocaine), LET (lidocaine, epinephrine and tetracaine), topicaine, morphine or similar local anesthetics and combinations thereof and a pharmacologically acceptable carrier. Any pharmacologically acceptable carrier may be used, including but not limited to water. The compounds of the invention are generally diluted in a solution of acetic acid or 0.09% sodium chloride.

Table 2 is summarizes some topical anesthetics that are particularly well suited for use in the present invention.

TABLE 2

Local Anesthetics[a]

| Anesthetics | Ingredients | Vehicle | Application time recommended | Occlusion required | FDA Approved | Maximum Dose or area[b] |
|---|---|---|---|---|---|---|
| Betacaine-LA ™ | Lidocaine: procaine: dibucaine[c] | Vaseline ointment | 60-90 | No | No | 300 cm$^2$ |
| ELA-max ™ | 4% lidocaine | Liposomal | 60 | No | Yes | 100 cm$^2$ (C) 600 cm$^2$ >10 kg (A) & (C) |
| ELA-max 5 ™ | 5% lidocaine | Liposomal | 30 | No | Yes | 100 cm$^2$ (C) 600 cm$^2$ >10 kg (A) & (C) |
| EMLA ™ cream | 2.5% lidocaine: 2.5% prilocaine | Oil in water | 60 | Yes | Yes | None reported20 g/200 cm$^2$ (A) (C > 7 years old and 20 kg) |
| Tetracaine gel | 4% tetracaine gel[c] | Lecithin gel | 60-90 | Yes | No | None Reported |
| Amethocaine ™ | 4% tetracaine | | 40-60 | Yes | No | 50 mg (A) |
| Topicaine[d] ™ | 4% lidocaine | Microemulsion | 30-60 | Yes | Yes | 600 cm$^2$ (A) 100 cm$^2$ (C > 10 kg) |
| S-caine ™ | 2.5% lidocaine | Oil in water | 30-60 | No | Phase III clinical trials | To be determined |

[a]Adapted from Friedman el al, "Topical Anesthetics Update" Dermatol. Surg. 27: 1019-1025 (2001)
[b]A = adults C = children
[c]Compounded. Proprietary anesthetic ELA-Max and ELA-Max 5 contain a liposomal delivery system of 4% or 5% lidocaine. This delivery system has multilamellar vesicles containing several lipid bilayers dispersed in an aqueous medium. Liposomes facilitate the entry of the anesthetic into the skin and can also provide a sustained release.

S-caine™ patch is a delivery system that utilizes an oxygen-activated heating system to increase the rate of anesthetic delivery. This patch may be used in the method of the present invention or the phycotoxin composition of the present invention may be formulated in such a patch. The commercially available S-caine™ patch contains a 1:1 eutectic mixture of lidocaine and tetracaine with a disposable heating element that generates a controlled level of heat (39-41 C) for two hours. The S-patch is effective in reducing the pain associated with shave biopsies and venipuncture. A related topical is the S-caine local anesthetic peel. The peel is a cream that dries into a flexible membrane that is readily removed. It is most effective on contoured regions of the body such as the face.

As can be seen from Table 2, these typical applications generally require the application of the topical formulation at least 30 minutes prior the beginning of any procedure. The addition of the phycotoxins greatly reduces the waiting period by providing a substantially immediate benefit, in addition to the later benefit provided by the anesthetic compound.

In another aspect of the invention the compositions of the present invention include at least one GTX compound in combination with one or more compounds such as analgesics, nonsteroidal anti-inflammatories (NSAIDS); antibiotics including amebicides, broad and medium spectrum, fungal medications, monobactams and viral agents; central nervous system drugs; minerals; immunomodulators; immunosuppressives; thyroid preparations; steroids and hormones; restalin (Restylane®) and other painful injections such as allergy medication injections, and vitamins selected from water-soluble vitamins such as B complex, vitamin C, vitamin B12 and folic acid and veterinary formulations.

In a more preferred aspect of the invention, analgesics include acetaminophen, ibuprofen, tluriprofen, ketoprofen, voltaren (U.S. Pat. No. 3,652,762), phenacetin and salicylamide. NSAIDS include naproxen, acetaminophen, ibuprofen, flurbiprofen, ketoprofen, phenacetin, salicylamide, and indomethacin. Antibiotics include amebicides, broad and medium spectrum, fungal medications, allergy medications, monobactams and viral agents and specifically including materials such as erythromycin, penicillin and cephalosporins and their derivatives; central nervous system drugs such as thioridazine, diazepam, meclizine, ergoloid mesylates, chlorpromazine, carbidopa and levodopa. Metal salts include potassium chloride and lithium carbonate. Minerals include iron, chromium, molybdenum and potassium. Thyroid preparations include synthetic thyroid hormone, and thyroxine sodium. Steroids and hormones include ACTH, anabolics, androgen and estrogen combinations, androgens, corticoids and analgesics, estrogens, glucocorticoid, gonadotropin, gonadotropin releasing, human growth hormone, hypocalcemic, menotropins, parathyroid, progesterone, progestogen, progestogen and estrogen combinations, somatostatis-like compounds, urofollitropin, vasopressin, and others; Vitamins include water-soluble vitamins such as B complex, vitamin C, vitamin B12 and folic acid and veterinary formulations. It should be understood by those of skill in the art that, subject to the conditions set forth with respect to the formula I above, other mixtures and combinations of tricyclic 3,4-propinoperhydropurines with the compounds described above, are within the scope of this invention.

Restalin or RESTYLANE® is a crystal-clear, biodegradable NASHA (Non-Animal Stabilized Hyaluronic Acid) gel, which is injected into the skin in order to add volume to lips and lift up wrinkles and folds. Restalin is considered to be safer than collagen injections, for example, to make the lips appear fuller. The FDA has recently approved Restylane®, as an injection for the correction of moderate to severe facial wrinkles and folds, such as nasolabial folds, the lines between the nose and mouth. However, such injections tend to be painful because they are often injected into areas containing many nerve endings. The current compositions help to reduce the pain of injection.

Similarly, venipuncture and the placement of an I.V. needle can be painful as well. Due to the rapid and safe action of the current composition, the waiting period between when the composition is applied and the effective numbing is greatly reduced.

Alternatively, the pharmaceutical compositions of the invention comprise at least one compound selected from the group consisting of saxitoxin (STX), neosaxitoxin, decarbamoylsaxitoxin and Botulin A toxin, along with at least one GTX compound, and optionally, two or more GTX compounds, as well as at least one other compound.

The present invention includes the use of toxins obtained or processed by bacterial culturing, toxin extraction, concentration, preservation, freeze drying, and/or reconstitution, as well as modified or recombinant toxins, and derivatives or fragments of toxins made by recombination.

Without being bound by theory, when applied locally, these compounds appear to carry out their antispasmodic action by blocking the spreading of nervous impulse, or neuronal transmission, by reversibly binding to the sole biological molecular receptor, i.e. the voltage gated sodium channel, present in all neurons and excitable cells. By binding to this channel, there is no entry of sodium to the neuronal cell; depolarization does not occur and, therefore, propagation of the impulse is stopped. This action mechanism blocks the presynaptic release of at least some of the neurotransmitter acetylcholine in the neuromuscular plate, thus interfering with neuromuscular transmission, paralyzing the muscle and preventing it from contracting, or producing a relaxation of muscles contracted by pathological problems. This mechanism is particularly efficient for cosmetic purposes, as it does not let some facial muscles contract, all of them associated with and responsible for the formation of wrinkles, thus producing the sought-after effect of facial rejuvenation.

The concentration of the active agent in the formulation can vary a great deal, and will depend on a variety of factors, including the condition to be treated, the desired effect, the ability and speed of the active agent to reach its intended target, and other factors within the particular knowledge of the patient and physician. Preferred formulations will typically contain a sufficient amount of the active agent to deliver a dose on the order of about 1-1000 units of the active agent to the treatment site. More preferably, the delivered dose is about 20-500 units of the active agent. Even more preferably, the delivered dose is more than 32 units up to about 1000 units of the active agent, and most preferably, the delivered dose is more than 40 units up to about 1000 units of the active agent, about 50-1000 units of the active agent, about 50-500 units of the active agent, or about 75-200 units of the active agent.

The pharmaceutical preparations of the invention are administered around the muscle or neuron that is to be paralyzed or prevented from contracting. This invention is not limited to specific drug delivery systems, device structures, enhancers or carriers, as such may vary. It is also to be understood that the terminology used herein is for the purpose of describing particular embodiments only, and is not intended to be limiting.

The present invention also relates to a composition for application by injection. The composition may be in any form suitable for injection. The composition of the present invention will comprise at least one phycotoxin, at least one additional compound and a pharmaceutically acceptable carrier. In a more preferred aspect, the composition of the present invention will comprise two or more phycotoxins along with at least one additional compound and a pharmaceutically acceptable carrier. The application by injection should be in amounts of no more than two milliliters in different places around the muscle, particularly around the areas of greatest innervations. When injected the effect is substantially immediate.

The transdermal effect of the compositions and methods of the invention is immediately apparent, generally occurring within a maximum of 30 seconds to five minutes after penetration of the active compound through the skin. The maximum effect is generally achieved within 15 minutes of penetration of the active compound through the skin. Its effective duration depends on the dose administered, the muscle in question, as well as the volume and specific composition administered. This is the pattern for all clinical applications and pathologies.

The topical or transdermal composition may be in any form suitable for application to the body surface, and may comprise, for example, a cream, lotion, solution, gel, ointment, paste or the like, and/or may be prepared so as to contain liposomes, micelles, and/or microspheres. The composition may be directly applied to the body surface or may involve use of a drug delivery device. Thus, a formulation or drug reservoir may be aqueous, i.e., contain water, or may be nonaqueous and used in combination with an occlusive overlayer so that moisture evaporating from the body surface is maintained within the formulation or transdermal system during drug administration. In some cases, however, e.g., with an occlusive gel, a nonaqueous formulation may be used with or without an occlusive layer.

Ointments are semisolid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in Remington: The Science and Practice of Pharmacy, $19^{th}$ Ed. (Easton, Pa.: Mack Publishing Co., 1995), at pages 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight; again, see Remington: The Science and Practice of Pharmacy for further information.

Creams are viscous liquids or semisolid emulsions, either oil-in-water or water-in-oil. Cream bases are water-washable, and contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

Gels are semisolid, suspension-type systems. Single-phase gels contain organic macromolecules distributed substantially uniformly throughout the carrier liquid, which is typically aqueous, but also, preferably, contain an alcohol and, optionally, an oil. Preferred "organic macromolecules," i.e., gelling agents, are crosslinked acrylic acid polymers such as the "carbomer" family of polymers, e.g., carboxypoiyalkylenes that may be obtained commercially under the Carbopol™ trademark. Also preferred are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Lotions are preparations to be applied to the skin surface without friction, and are typically liquid or semiliquid preparations in which solid particles, including the active agent, are present in a water or alcohol base. Lotions are usually suspensions of solids, and preferably, for the present purpose, comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like.

Pastes are semisolid dosage forms in which the active agent is suspended in a suitable base. Depending on the nature of the base, pastes are divided between fatty pastes or those made from a single-phase aqueous gels. The base in a fatty paste is generally petrolatum or hydrophilic petrolatum or the like. The pastes made from single-phase aqueous gels generally incorporate carboxymethylcellulose or the like as a base.

Formulations may also be prepared with liposomes, micelles, and microspheres. Liposomes are microscopic vesicles having a lipid wall comprising a lipid bilayer, and can be used as drug delivery systems herein as well. Liposome preparations for use in the instant invention include cationic (positively charged), anionic (negatively charged) and neutral preparations. Cationic liposomes are readily available. For example, N[1-2,3-dioleyloxy)propyl]-N,N,N-triethylammonium (DOTMA) liposomes are available under the tradename Lipofectin™. (GEBCO BRL, Grand Island, N.Y.). Similarly, anionic and natural liposomes are readily available as well, e.g., from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with DOTMA in appropriate ratios. Methods for making liposomes using these materials are well known in the art.

Micelles are known in the art as comprised of surfactant molecules arranged so that their polar headgroups form an outer spherical shell, while the hydrophobic, hydrocarbon chains are oriented towards the center of the sphere, forming a core. Micelles form in an aqueous solution containing surfactant at a high enough concentration so that micelles naturally result. Surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethylammonium chloride, dodecylammonium chloride, polyoxyl 8 dodecyl ether, polyoxyl 12 dodecyl ether, nonoxynol 10 and nonoxynol 30. Micelle formulations can be used in conjunction with the present invention either by incorporation into the reservoir of a topical or transdermal delivery system, or into a formulation to be applied to the body surface.

Microspheres, similarly, may be incorporated into the present formulations and drug delivery systems. Like liposomes and micelles, microspheres essentially encapsulate a drug or drug-containing formulation. They are generally although not necessarily formed from lipids, preferably charged lipids such as phospholipids. Preparation of lipidic microspheres is well known in the art and described in the pertinent texts and literature.

Various additives, known to those skilled in the art, may be included in the compositions. For example, solvents, including relatively small amounts of alcohol, may be used to facilitate solubilization of the active agent. Other optional additives include opacifiers, antioxidants, fragrance, colorant, gelling agents, thickening agents, stabilizers, and the like. Other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof.

The transdermal compositions of the invention may be administered to a predetermined area of the patient's body surface in combination with a permeation enhancer and/or a permeation enhancing treatment. One class of suitable permeation enhancers are chemical permeation enhancers, such as a hydroxide-releasing agent in an amount effective to enhance the flux of the agent through the body surface without causing damage thereto, or in combination with an ultrasound treatment. Other suitable chemical permeation enhancers are described in, for example, W. R. Pfister and D. S. T. Hsieh, "Permeation Enhancers Compatible with Transdermal Drug Delivery Systems, Part I: Selection and Formulation Considerations," *Pharm. Technol.*, September 1990, and W. R. Pfister and D. S. T. Hsieh, "'Permeation Enhancers Compatible with Transdermal Drug Delivery Systems, Part II: System Design Considerations," *Pharm. Technol.*, October 1990, the disclosures of which are hereby incorporated by reference to describe suitable chemical permeation enhancers. Exemplary chemical permeation enhancers for use in the present invention include, but are not limited to, alcohols, amines and amides, such as urea, amino acids, amino acid esters, Azone®, pyrrolidones, terpenes, fatty acids, fatty acid esters, macrocyclic compounds, tensides, sulfoxides, liposomes, transferomes, lecithin vesicles, ethosomes, water, anionic, cationic and non-ionic surfactants, polyols and essential oils.

The GTX compounds of the present invention are typically small molecules having relatively low molecular weights, are water-soluble and have a positive charge associated with the compounds and thus are cationic. Ideally, transdermal penetration is carried out using small molecules that are fat-soluble and have a neutral charge. Thus, in the present case, it may be desirable, under certain circumstances, to employ anionic chemical permeation enhancers and/or anionic surfactants to improve the transdermal delivery of the GTX compounds. Also, since fat solubility may improve transdermal delivery, it may be desirable to chemically modify the GTX compounds to change their hydrophilic-lipophilic balance (HLB) and render them more fat-soluble. One example of such a modification might be to add a lipophilic "tail" to the GTX molecule by, for example, attaching a long chain fatty molecule to the GTX molecule in any suitable, conventional manner.

Thus, the present method of transdermally delivering the active agent may vary, but necessarily involves application of a composition containing a tricyclic 3,4-propinoperhydropurine to a predetermined area of the skin or mucosal tissue for a period of time sufficient to provide an effective blood level or penetration level of active ingredient(s). The method may involve direct application of the composition as an ointment, gel, cream, or the like, or may involve use of a drug delivery device as taught in the art, e.g., in U.S. Pat. Nos. 4,915,950, 4,906,463, 5,091,186 or 5,246,705, the disclosures of which are hereby incorporated by reference for the purpose of describing specific transdermal drug delivery devices, or as described below.

In another embodiment of the present invention, a physical transdermal permeation enhancement method selected from iontophoresis, phonophoresis, sono-macroporation, thermal modulation, magnetic modulation, and mechanical modulation, may be employed either alone, or in combination with another physical or chemical permeation enhancer. Examples of most of these methods can be found in, for example, "Drug Permeation Enhancement, Theory and Applications," D. S. T. Hsieh, ed., Marcel Dekker, New York, N.Y. (1994).

Iontophoresis can deliver the toxin to a subdermal site by passing electrical current across a patch or skin area containing a composition comprising the toxin. In certain embodiments, an electrode may be place on the external surface of a transdermal patch or on the skin, and a ground electrode is placed elsewhere. Current is applied to cause the toxin to penetrate the skin. The amount of current is typically less than 1 $mA/cm^2$ and preferably 0.3 to 0.7 $mA/cm^2$ are employed. Since the various GTX's have a +1 charge, this facilitates penetration into the skin both, in comparison to other molecules having a +2 charge, for example, but also via the application of intophoresis.

Particularly preferred methods of permeation enhancement are phonophoresis and sono-macroporation. These methods offer several advantages including bypassing the gastrointestinal degradation and hepatic first-pass metabolism encountered in oral administration of medicaments, improves patient compliance since it is non-invasive, may eliminate the need to use chemical permeation enhances which can damage the skin, can be used to deliver the active ingredients in ionic or non-ionic form, works well with both aqueous and non-aqueous carriers, can deliver the actives to deep subcutaneous tissues, and these methods can be used in combination with other transdermal delivery systems such as transdermal patches, and/or permeation enhancers. Phonoporesis has been used to deliver local anesthetics in, for example, E. J. Novak, Arch. Phys. Med. Rehabil., May, 231 (1964), and H. A. E. Benson, J. C. McElnay, and R. Harland, Int. J. Pharm., 44, 65 (1988). Suitable conditions for phonoporesis are described in, "Y. Sun and J. C. Liu, "Transdermal Drug Delivery by Phonoporesis: Basics, Mechanisms, and Techniques of Application, Chapter 15, "Drug Permeation Enhancement Theory and Applications, D. S. T. Hsieh, Ed., Marcel Dekker, New York, N.Y. (1994), the disclosure of which is hereby incorporated by reference for the purpose of describing suitable phonoporesis conditions.

If phonoporesis is to be employed, the composition should contain a suitable coupling agent for transfer of acoustic energy from the surface of the transducer to a patient. Water is a preferred coupling agent since there is only a small difference between the acoustic impedance of water and that of soft tissue. Alternatively, commercially available coupling agents, such as aqueous thixotropic gels, glycerol, and mineral oil, may be employed.

In carrying out phonoporesis, frequencies of from about 10 kHz to about 20 MHz may be employed. More preferably, frequencies of from about 1 MHz to about 16 MHz are used. The ultrasound may be continuous or pulsed and the intensity and duration of the treatment can be determined by a person skilled in the art pending on the patient and the desired level of drug delivery required. Typically, intensities of less than about 2 $W/cm^2$ are applied in phonoporesis.

Alternatively, sono-macroporation may be employed. If sono-macroporation is employed, typically acoustic intensities of more than 2 $W/cm^2$ up to about 40 $W/cm^2$ will be employed in combination with frequencies of about 10-100 kHz, more preferably, 20-80 kHz. Sono-macroporation is most useful for enhancing the permeation of larger molecules having molecular weights of about 400-600 kDa.

The foregoing compositions and delivery methods can be employed to carry out the various methods of the present invention, if desired. Thus, any of the described compositions can be employed to treat any of the various ailments, muscle disorders or other conditions that are described herein.

In the following examples, "dose" refers to the amount of toxin used during one administration to a patient. A dose may be applied to one or more sites. "Treatment" refers to the total number of doses given to a patient to achieve the desired effect. 100 units of the mixture of GTX 2 and GTX 3, determined by mouse assay, is equivalent to 25 µg of GTX 2 and GTX 3, as determined by HPLC-FLD.

EXAMPLE 1

One unit of activity corresponds to an amount of the composition of the invention necessary to block the muscular contractions of the crural biceps of a 20 gram CFI albino BALB-C strain mouse leg for 1.5 to 2.0 hours. The toxin was intramuscularly injected in the crural biceps of the mouse right leg in a volume of 0.5 ml. The left leg is used as a control. This was done in three mice and the paralyzing effect was tested every 30 minutes for the first two hours, and then every 2, 4, 8 hours and overnight. Depending on the dose injected, the paralyzing effect can last 24 hours or longer. This example confirms the reversible nature of the effect of the toxins of the present invention and demonstrates that the duration of the effect can be controlled by varying the dosage of the toxins.

EXAMPLE 2

Fibromyalgia

Figure 1:
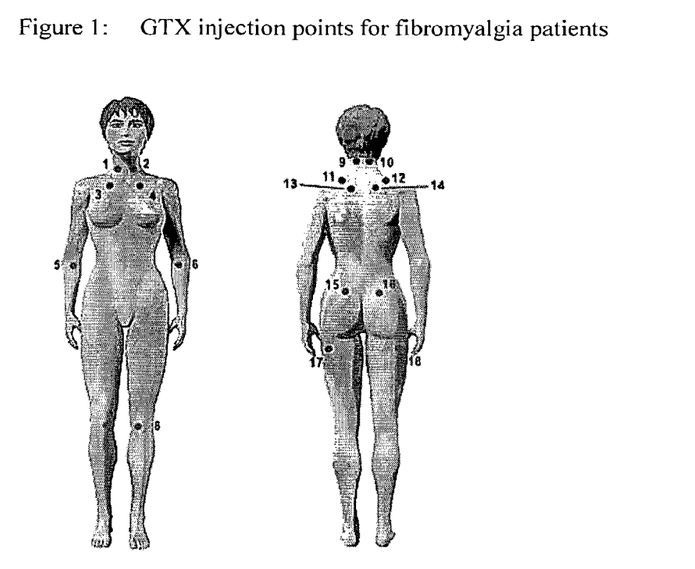
FIG. 1 is a diagram showing the gonyautoxin (GTX) injection points for fibromyalgia patients.

Each dose of toxin contains from 10 to 400 units of activity of a mixture of gonyautoxins (GTX2/GTX3) and is intramuscularly infiltrated locally in 2 to 20 muscle points according to the diagram shown in FIG. 1. Each injection point receives 0.1 to 0.2 ml (10 to 20 units) of toxin solution, which contains 100 units of activity of the mixture of GTX2/GTX3 per milliliter of solution. The carrier is 0.9% sodium chloride in sterile solution, without preservatives. This dose may be repeated, for example, every four weeks, as prescribed by the physician, or according to the patient's requirements in order to minimize pain.

10 patients have been enrolled in an open label study. The patients need to fulfill specified clinical criteria. Upon evaluation and admission to the study, the patients are administered the toxin as described above. Depending on the symptomatology and local painful points of each patient, the physician determines the number of infiltration points, following the general injection site scheme shown in FIG. 1. All 10 patients reported complete relief of pain, starting 20 minutes after each administration. The patients have been followed up for a period of three months after a single administration and only 2 patients had relapsed with painful symptoms at 4 and 8 weeks after the treatment.

EXAMPLE 3

Tension Headache (Tension Cefelea)

Figure 2:
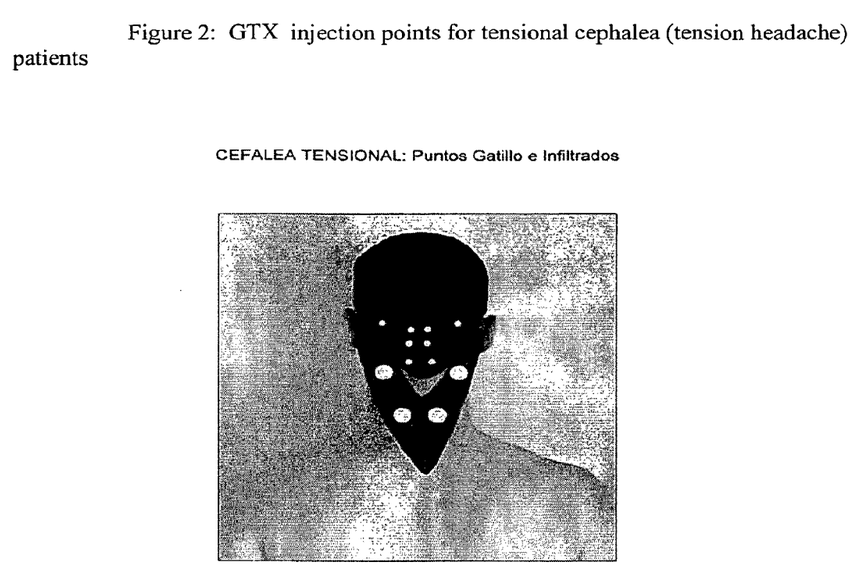
FIG. 2 is a diagram showing the gonyautoxin (GTX) injection points for patients suffering from tension headache.

Each dose of toxin contains from 10 to 400 units of activity of a mixture of gonyautoxins (GTX2/GTX3) and is intramuscularly infiltrated locally in 2 to 10 muscle points according to the diagram shown in FIG. 2. Each injection point receives 0.1 ml (10 units) of a toxin solution, which contains 100 units of activity of the mixture of GTX2/GTX3 per milliliter of solution. The carrier is 0.9% sodium chloride in a sterile solution, without preservatives. This dose may be repeated, for example, every four weeks, as prescribed by the physician, or according to the patient's requirements.

20 patients have been enrolled in an open label study. The patients need to fulfill the following clinical criteria: they have to be chronic patients, that experience primary nonvascular, tensional headache at least twice a week, and that have been treated previously for this condition with analgesics, systemic muscle relaxants, local corticosteroid infiltration, or antidepressants. Upon evaluation and admission to the study, the physician determines the number of injection points for the toxin, basically following the general injection site scheme described above in reference to FIG. 2.

Results indicate that all 20 patients reported complete relief of pain, starting 20 minutes after the administration. The patients have been followed up for a period of about 3 months after a single administration. To date, only 4 of the patients have experienced a relapse of minor pain from tension headache, 4 to 6 weeks after treatment.

EXAMPLE 4

Blepharospasm and Hemifacial Spasm

Each dose of toxin contains from 10 to 400 units of activity of a mixture of gonyautoxins (GTX2/GTX3) and is intramuscularly infiltrated locally in the orbital muscles via 2 to 4 injection points. Additional local injection points can be employed in other face muscles, as determined by the physician, and/or according to the severity of the pathology in each patient. Each injection point receives from 0.1 to 0.4 ml (10 to 40 units of activity) of toxin solution, which contains 100 units of activity of a mixture of GTX2/GTX3 per milliliter of solution. The carrier is 0.9% sodium chloride in a sterile solution, without preservatives. This dose may be repeated every 2-4 weeks, as prescribed by the physician, or according to the patient's requirements.

A few volunteers have been treated for blepharospasm and/or hemifacial spasm. Depending on the symptomatology of the patient, the physician determines the number of injection points (2 to 20).

Figure 3A:
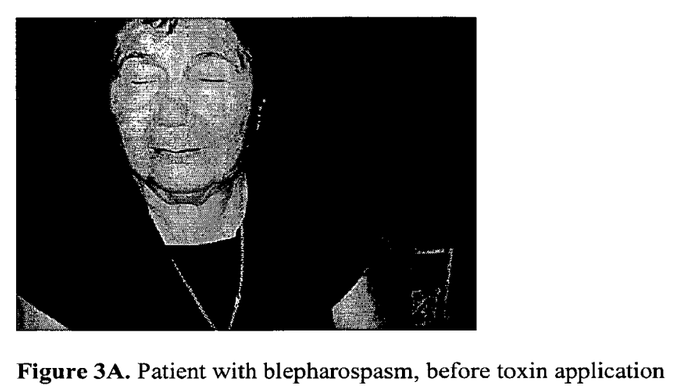
FIG. 3A is a picture showing a patient suffering from blepharospasm before GTX treatment.
Figure 3B:
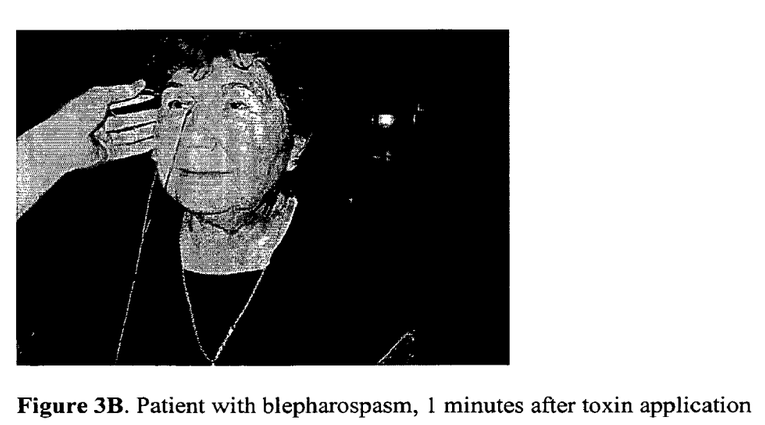
FIG. 3B is a picture showing a patient with blepharospasm after treatment with GTX.

FIGS. 3A and 3B show the effect of the local injection of the GTX toxin in a blepharospasm patient. In FIG. 3A, the patient has the eyelid contracted and the eyes closed, characteristic of the blepharospasm pathology. After two minutes post injection, the patient could open the eyes, and the spasm relaxed (FIG. 3B). This effect lasted 2 weeks.

Figure 4A:
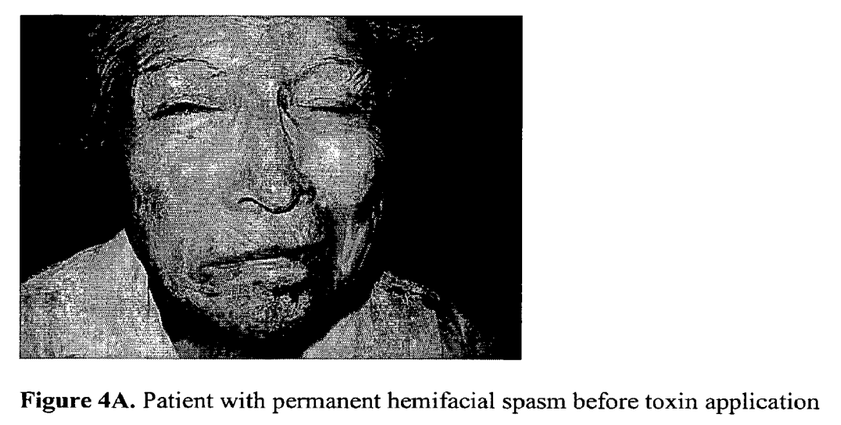
FIG. 4A is a picture showing a patient suffering from a permanent hemifacial spasm before GTX treatment.
Figure 4B:
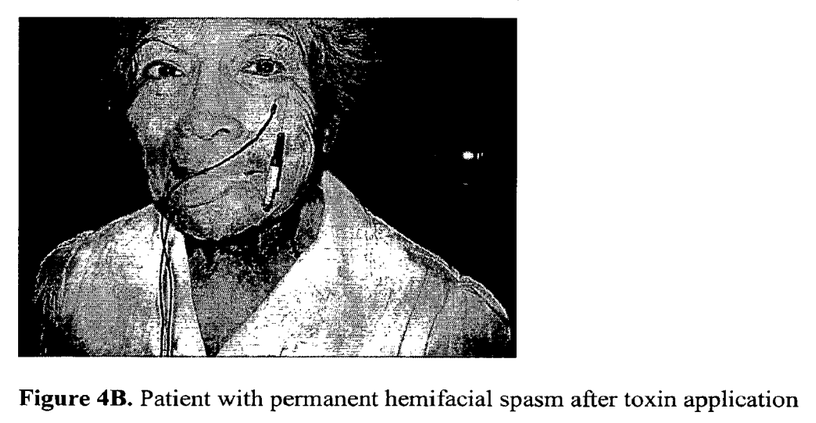
FIG. 4B is a picture showing a patient with a permanent hemifacial spasm after GTX treatment.

FIG. 4A shows a patient with permanent hemifacial spasm that was Botulinum toxin A resistant. The GTX toxin was administered as described above. After two minutes post injection, the face muscles relaxed as shown in FIG. 4B. This effect lasted 1 week.

EXAMPLE 5

Cosmetic Gel for Treatment of Wrinkles

| | |
|---|---|
| Ethoxydiglycol | 6.500% w/w |
| Laureth-7 | 1.000% w/w |
| Diazolidinyl urea | 0.300% w/w |
| Methylparaben | 0.150% w/w |
| Propylparaben | 0.050% w/w |
| Hydroxyethyl cellulose | 1.500% w/w |
| Toxins GTX2/GTX3 | 0.01-0.0001% w/w |
| Water | to 100% w/w |

Purpose of ingredients:
Ethoxydiglycol: Penetration-enhancer (organic solvent)
Laureth-7: Penetration enhancer (surfactant)
Diazolidinyl urea, Methylparaben, Propylparaben: Preservatives
Hydroxyethyl cellulose: Thickener Compounding Procedure:
PCT/US2005/015946

Dissolve all ingredients, except for hydroxyethyl cellulose, in water and mix to make a clear, uniform solution. Disperse the hydroxyethyl cellulose polymer with vortex mixing and continue mixing without vortex until a smooth, clear gel forms.

EXAMPLES 6-8

Creams for Topical Administration

| Cream N° 1 | |
|---|---|
| Ingredient | % w/w |
| Water to | 100.00 |
| Propylene glycol | 5.00 |
| Glyceryl monostearate | 4.50 |
| Squalene | 4.50 |
| Propylene glycol dicaprylate/caprate | 4.00 |
| Cyclomethicone | 3.00 |
| Cetyl lactate | 2.50 |
| DMDM hydantoin (and) Iodo propynyl butyl carbamate | 0.15 |
| Glyceryl stearate/PEG 100 stearate | 0.80 |
| PVM/MA decadiene crosspolymer | 0.25 |
| Triethanolamine | 0.16 |
| Alpha tocopherol (and) ascorbyl palmitate (and) lecithin (and) glyceryl stearate (and) glyceryl oleate (and) citric acid | 0.05 |
| EDTA disodium | 0.02 |
| Toxins GTX2/GTX3 | 0.01-0.0001 |

| Cream N°2 | |
|---|---|
| Ingredients | % w/w |
| Water to | 100.00 |
| Polyglyceryl methacrylate | 5.00 |
| Hydrogenated polyisobutene | 5.00 |

-continued

| Cream N°2 | |
|---|---|
| Ingredients | % w/w |
| Propylenglycol | 5.00 |
| Propylenglycol dicaprylate/caprate | 4.00 |
| Cetylic alcohol | 3.00 |
| Cyclomethicone | 2.00 |
| Diazolidinyl urea (and) methylparaben (and) propylparaben (and) propylene glycol | 1.00 |
| Cetearylic alcohol (and) ceteareth 20 | 0.70 |
| Methyl glucose dioleate | 0.50 |
| Triethanolamine | 0.28 |
| Alpha tocopherol (and) ascorbyl palmitate (and) lecithin (and) glyceryl stearate (and) glyceryl oleate (and) citric acid | 0.05 |
| EDTA disodium | 0.02 |
| Toxins GTX2/GTX3 | 0.01-0.0001 |

| Cream N° 3 | |
|---|---|
| Ingredients | % w/w |
| Water to | 100.00 |
| Glyceryl distearate (and) PEG-150 stearate (and) glyceryl stearate (and) cetearylic alcohol (and) cetylic alcohol (and) stearic acid | 5.30 |
| Glycerine | 2.00 |
| Dicaprylyl carbonate | 2.00 |
| Diazolydinyl urea (and) Iodo propynyl butyl carbamate | 1.00 |
| Dimethicone | 0.50 |
| Sodium polyacrylate | 0.35 |
| Cetylic alcohol | 0.30 |
| Alpha tocopherol (and) ascorbyl palmitate (and) lecithin (and) glyceryl stearate (and) glyceryl oleate (and) citric acid | 0.05 |
| Triethanolamine | 0.05 |
| EDTA disodium | 0.02 |
| Toxins GTX2/GTX3 | 0.01-0.0001 |

EXAMPLE 9

Ointment

| Petrolatum | 75.000% w/w |
|---|---|
| Sorbitan sesquioleate | 10.000% w/w |
| White Wax | 10.000% w/w |
| Toxins GTX2/GTX3 | 0.01-0.0001% |
| Water | to 100% |

Purpose of Ingredients:
Petrolatum: Emollient ointment base
Sorbitan sesquioleate: Emulsifier, penetration enhancer
White Wax: Thickener, Stabilizer Compounding Procedure:

Melt the petrolatum, sorbitan sesquioleate and white wax at 60 degrees C. and mix until uniform. Slowly incorporate the aqueous solution of toxin and continue mixing until the ointment congeals.

EXAMPLE 10

A cream formulation containing a mixture of GTX2/GTX3 was applied to the forehead (glabellar or frown lines) and around the eyes (crow feet wrinkles) of a healthy adult volunteer. After application, the area was treated for 30 seconds with a handheld sonicator (Beauty Care System, Model JS-2000, Annapolis, Md. USA) to accelerate transdermic absorption. The application of the cream induced reduction of wrinkles that lasted over 24 hours.

EXAMPLE 11

Doses of 200 units up to 5,000 units of a mixture of GTX 2 and GTX 3, as employed in example 2, have been administered by injection in the internal anal sphincter, in normal volunteers. These doses were well tolerated, without adverse or negative side effects. The volunteers remained healthy during and after the local injection of this relatively large amount of toxins.

EXAMPLE 12

Ten healthy male adults between 24 and 48 years old with normal sphincter tone (pressure at rest less than 72 mmHG as determined by anorectal manometry) were studied. The test subjects had no anorectal pathologies like hemorrhoids, fistula or abscesses. Before intervention, tests were performed including anorectal manometry, electromyography, a hemogram, a basic metabolic panel and a urinalysis.

A dosage of 100 units of activity of a combination of GTX-2 and GTX-3, in approximately a 2:1 ratio, in a total volume of 1.0 ml was locally infiltrated into both sides of the anal internal sphincter (0.5 ml each side) with an insulin syringe (25 gauge). The mixture of GTX-2 and GTX-3 was purified from shellfish collected in the Chilean Patagonia fjord that was found to be highly-contaminated with PSP toxins using standard purification methods.

Two minutes post injection an anorectal manometry was performed. Resting and voluntary contraction pressures were measured and recorded and compared to the baseline measurements. Recto-anal and cortical-anal reflexes were also measured and recorded in each participant before and after toxin injection. The anal canal pressure was recorded by a stationary pull-through technique with a water-filled microballoon and external transducer (PVB) perfusion equipment. Recording and analysis of the tracing were made by a computerized system (8 channels polygraph ID, Metronic Polygraph with Polygram 98 ver. 2.2).

Anal resting pressures were recorded in millimeters of mercury with the stationary pull-through technique and the computer identified the mean pressure. The maximal voluntary contraction was assessed by evaluation of the voluntary contractions of the anal sphincter in each participant. Amplitude was expressed in milliliters of mercury.

The participants were evaluated at 24 and 48 hours, after one week and after 12 days. Blood and urine samples were collected from each participant a week after the injection for laboratory analysis. Toxin levels in the urine were measured 4 hours after injection. Pulse and blood pressure, as well as any side effects and pain scores were recorded at each visit. The injection pain scores and the pain two minutes after the injections were determined by consulting the participants using a 1-10 pain scale, with 10 being the maximum value of pain.

Long-term outcomes were determined after a median follow up of 12 months via personal communication with the participants and by clinical examination at the request of the participants.

No participant dropped out of the study and none had any adverse or negative side effects. Laboratory tests did not show any significant changes and no toxin was detectable in the urine samples collected 4 hours after injection. Toxin detection was performed by analytical high performance liquid chromatography (HPLC) with on line fluorescent detection; the detection limit of this method is 1 microgram in 10 ml. This also corresponds to the fact that PSP toxins, once injected, immediately enter the extracellular medium producing a dilution.

Table 1 is a summary of the test results. As shown in Table 1, all participants showed anal sphincter relaxation within 30 seconds after injection, as determined by clinical anorectal examination during the injection and then after two minutes using anorectal manometry. The participants all stated that they felt the anal anesthesia for an 15 average time of 59.5 minutes±7.12 minutes (mean value±Stand. Dev.) and sphincter hypotonical sensation for 40.0±4.20 minutes. None of the participants showed flatus incontinence or transitory fecal incontinence.

TABLE 1

| Symptoms and Side Effects | |
|---|---|
| Healthy Voluntary Adults | 10 |
| Pain During Injection (On a scale of 1-10) | 5.55 ± 0.4 |
| Pain 2 Minutes Post Injection | 100% without pain |
| Anal Anesthetic Sensation (time) | 59.50 ± 7.12 minutes (n = 9) |
| Sphincter Relaxation Sensation | 40.0 ± 4.20 minutes (n = 9) |
| Flatus Incontinence | None |
| Fecal Incontinence | None |
| Clinical Evaluation | Immediate Relaxation |
| Side Effects | None |
| Other | All asymptomatic after 24 hours |

Table 2 is a summary of the anorectal manometric recordings. Manometric recording showed a significant decrease in the anal maximal voluntary contraction pressure. Two minutes after injection the pressure was 55.2±6.2% (mean value±standard dev.) of the base line values, a diminishing of 44.8%. Twenty-four hours after injection, the drop in the anal maximal voluntary contraction pressure increased to 53% of the baseline value. Fifteen days after injection all of the anal maximal voluntary contractions had returned to the base line values. Electromyography (EMG) recorded before the injection and after the injection indicated that the injection nearly eliminated muscle activity. At the 12-month follow up examination (long term follow-up) none of the participants showed any adverse or systemic side effects (i.e. anorectal problems).

TABLE 2

| Anorectal Manometry Recordings | |
|---|---|
| Maximum Resting Pressures | 66 ± 5.8 mmHg (n = 10) |
| Maximum Voluntary Contraction Pressure (MVCP) | |
| Pre-Injection | 126 ± 11.5 mmHg (n = 10) |
| 2 minutes Post-Injection | 69.5 ± 5.8 mmHg (n = 10) |
| 24 hours Post Injection | 59.2 ± 7.2 mmHg (n = 5) |
| % MVCP 2 Minutes Post-Injection | 55.2 ± 6.2% (n = 9) |
| % MVCP 24 Hours Post-Injection | 47.0 ± 6.8% (n = 5) |
| Recto-Anal Reflex (after 60 cc) | 100% Retention |
| Cortical-Anal Reflex | 100% Retention |

As can be seen from Table 2, complete anal sphincter relaxation after administration of the mixture of GTX-2 and GTX-3 was achieved in 100% of the participants immediately. This indicates that the injection of these toxins locally produces paresis in the sphincter. This relaxation was confirmed by anal clinical evaluation as performed by coloproctologists during the injection. The injection of the toxin did not produce any long lasting side effects such as flatus or fecal incontinences and the recto-anal and cortical-anal reflexes remained normal. The toxin level injected blocks extra contraction of the muscle but leaves sufficient strength to provide for normal performance.

The local peripheral application of toxins interferes with neuromuscular transmission, altering the action potential which results in a temporarily paralysis of the sphincter. The mode of action of GTX is directed to the injected muscle leaving other muscles in the area unaffected. The paretic effects indicate that local injection of the sphincter lasts for 12 days. As there are no side effects, the use of this toxin injected locally is safe and effective particularly for use in the anal sphincter. The immobilization of healing tissue is a fundamental therapeutic principle and treatments using paralytic toxins may be effective in the remission of other muscle-related pathologies such as those described above.

EXAMPLE 13

Fifty adults between the ages of 18 and 70 with symptomatic anal fissures were evaluated for inclusion in a study to test the effects of GTX local infiltration efficacy in the treatment of anal fissure via the reduction of anal tone to promote the healing process and eliminate the need for surgical intervention as well as provide a safe and effective alternative to ointment treatments.

Patients were evaluated for the following inclusion criteria: evidence of anterior, posterior or both circumscribed ulcers, induration at the edges and posterior of horizontal fibers of the interior anal sphincter, with symptoms of post defecatory or permanent pain, bleeding or both. Patients with an anal fissure history of two or month duration were considered to be chronic. Table 3 contains a detail of the patients selected for study. Patients younger than 18 or older than 70 years of age were excluded from this study as were those patients that were pregnant or had anal fissure associated with other conditions such as hemorrhoids, fistula or anal abscess.

TABLE 3

Anal Fissure Patient Characteristics

| Characteristic | Patients (N = 50) |
|---|---|
| Sex (M/F) | 17/33 |
| Mean Age (Years) | 35.9 ± 13.1 |
| Spontaneous Pain (No. of Patients) | 46 |
| Post-defecatory Pain (No. of Patients) | 50 |
| Bleeding (No. of Patients) | 49 |
| Mean Duration of Symptoms (Months) | 24.4 ± 39.7 |
| Acute/Chronic | 17/33 |
| Localization (Posterior/Anterior/Bilateral) | 32/8/5 |
| History of Constipation (No. of Patients) | 42 |
| Previous Conservative Treatment (No.) | 36 |
| Previous Surgical Treatment (No.) | 2 |

The healing criteria and primary end points of the study were pain relief and fissure epithelization. The participants were fully informed about the action and mechanism of GTX and all included patients supplied their written consent. The study was a randomized double-blind trial in which the patients were diagnosed and injected with a mixture of GTX-2 and GTX-3 or placebo solution of 0.9% sodium chloride. The study was opened for humanitarian and ethical reasons after 15 placebo treated patients showed either no improvement or a worsening of their conditions and patients injected with GTX showed marked improvement after three weeks treatment.

The test dosage consisted of 100 units of activity of a mixture of GTX-2 and GTX-3 in 1.0 ml volume, which was locally infiltrated into both sides of the anal fissure, in the internal anal sphincter, in equal volumes. The injection was accomplished with an insulin needle (25 gauge).

Anal pressures were measured and recorded as described above. Patents were clinically evaluated after 7, 14 and 28 days post-injection. Pain during injection and two minutes were evaluated by asking the patients to rate their pain on a scale of 1 to 10, with 10 being the maximum pain value. No stool softeners, bulk laxatives or sitz baths were prescribed. Long-term outcomes where determined at the 12 month follow-up examination.

TABLE 4

Symptoms and Side-Effects in Patients After Treatment

| | |
|---|---|
| Number of Doses Needed | 2.6 ± 1.3 |
| Mean Healing Time (Days) | 17.6 ± 9.0 |
| Pain During Injection | 5.8 ± 2.3 |
| Pain 2 minutes Post Injection | 1.6 ± 1.2 |
| Duration of Bleeding (Post 1$^{st}$ Injection, Days) | 1.2 ± 0.9 |
| Duration of Pain (Post 1$^{st}$ Injection, Days) | 2.1 ± 0.7 |
| Flatus Incontinence | None |
| Fecal Incontinence | None |
| Digital Exam (Immed. Sphincter Relax) | 100% |
| Side Effects | None in 100% of Patients |

TABLE 5

Anorectal Manometry Recordings

| Maximum Resting Pressures (MRP) (N = 50 patients) | |
|---|---|
| Before Injection | 108.8 ± 24.9 |
| 2 Minutes Post Injection | 61.1 ± 22.8 |
| % MRP 2 Minutes Post Injection | 56.2 ± 12.5 |
| Maximum Voluntary Contraction Pressures (MVCP) (N = 50 patients) | |
| Pre-Injection (mmHg) | 159.9 ± 32.8 |
| 2 minutes Post Injection | 118.8 ± 12.7 |
| % of MVCP 2 minutes Post Injection | 74.3 ± 13.1 |
| Reflexes | |
| Recto-Anal (% Maintained) | 100 |
| Cortical (% Maintained) | 100 |

None of the fifty patients enrolled in the study had any adverse or negative side effects during or after the trial. As shown in Table 5, 100% of the patients showed immediate post-injection anal sphincter relaxation as detected by digital examination and anorectal manometry. During the digital examination, coloproctologists detected the anal tone reduction and all the patents declared that they felt anal anesthesia after injection. The seven day post-injection examination showed greatly reduced anal tone in all patients. No incontinence was observed and all the patients maintained the recto-anal and cortical-anal reflexes (see Table 4).

Table 5 demonstrates a significant decrease in the maximum resting pressures (MRP) in all the patients as indicted by the manometric recordings. The MRP recordings fell from 108.8±24.9 to 61.1±22.8 mmHg (Mean value±Standard Deviation) decreasing 15 to 56.2±12.5 of MRP baseline values. This represents a mean reduction of 43.8%. Similarly, maximum voluntary contraction pressure (MVCP) decreases to 74.3±13.1 of MVCP baseline values, a 25.7% mean reduction.

Patients with acute anal fissures stopped bleeding within 48 hours of injection. By the day seven post-injection examination, these patients showed epithelization of the lesion with modest pain only after defecation. At the day 14 post-injection examination, the patients all showed totally epithelization with scar formation.

Patients with chronic anal fissures also stopped bleeding within 48 hours. By the day seven post-injection digital examination, 50% of the patients with chronic anal fissures showed epithelization similar to the acute patients. Nevertheless, epithelization was evident by the 14-day post-injection examination and epithelization was complete by the 28-day post-injection examination in 98% of the patients with chronic anal fissure. All patients were post-defecation pain free and asymptomatic.

One patient relapsed 3 months post-injection and required surgical intervention. This patient was a 59 year old female with an eight year history of recurrent anal fissures accompanied with periods of intense pain and bleeding, which was further complicated with sub-fissural infiltration and bleeding tendency. Her anorectal manometry reading at baseline showed an MRP of 118 mmHg and a MVCP of 171 mmHg. The remaining patients in the study remained asymptomatic and healthy. After a 38 month follow-up, only two patients had presented a recurrence of the anal fissure requiring a different treatment.

The results indicate that 100% of the patients experienced relaxed anal sphincter immediately after infiltration. Paresis is produced in the internal sphincters and a concurrent reduction of anal tone is provided. Neither flatus or fecal incontinences were observed and all patients maintained functional anal and cortical-anal reflexes suggesting that infiltration blocks extra contraction of the muscle but leaves sufficient strength for normal muscle performance. Repeated injections did not produce any problems or side effects. The paretic effect lasts for more than a week. At the 12-month examination, no side effects were observed.

Of the fifty patients in the study, 3 of the acute and 33 of the chronic patients had been previously conservatively treated with sitz baths, stool softeners, high fiber diets, bowel regulation and topical ointments to no effect (not cured). The healing rate of this study was 98% within 28 days for all patients, but the 17 acute patients were healed within 15 days. These results show a higher efficacy than other pharmaceutical treatments (BoTox, nitroglycerine or nifedipine).

This example emphasizes that GTX treatment produces substantially immediate, and relatively long lasting muscle relaxation effects which can be beneficially employed to treat a variety of conditions. GTX treatment reduces the chemical denervation induction time period. GTX, when given in a 100 units of activity dosage, yields a reversible chemical denervation of twelve days duration, in contrast to BoTox treatment which produces an irreversible chemical denervation of three months or more duration along with proteolytic structural damage. Muscle inactivation persists until new fibrils grow from the nerve forming new junction plates at new areas on the muscle cell wall.

EXAMPLE 14

One unit of activity corresponds to an amount of the composition of the invention necessary to block the muscular contractions of the crural biceps of a 20 gram CF1 albino strain mouse leg for 1.5 to 2.0 hours. The toxin was intramuscularly injected in the crural biceps of the mouse right leg in a volume of 0.5 ml. The left leg is used as a control. This was done in three mice and the paralyzing effect was tested every 30 minutes for the first two hours, and then every 2, 4, 8 hours and overnight. Depending on the dose injected, the paralyzing effect can last 24 hours or longer. This example confirms the reversible nature of the effect of the toxins of the present invention and demonstrates that the duration of the effect can be controlled by varying the dosage of the toxins.

EXAMPLE 15

Hyperhydrosis

Two patients have been treated for palmar hyperhydrosis. Depending on the symptomatology, the physician determines the number of injection points for the toxin, basically following a general injection scheme in the fingers and palm. Each dose of toxin consists 10 to 400 units of a mixture of GTX 2/GTX 3 locally intramuscularly infiltrated in 2 to 10 muscle points. Each injection point receives 0.1-0.2 ml (10-20 units) of a toxin solution which contains 100 units GTX2/GTX3 per ml. The solution is made with 0.9% sodium chloride in a sterile solution, without preservatives.

The results show a decrease in the amount of sweating of the palm, as measured by determining the weight of a filter paper positioned for 5 minutes under the palm of the hand in the treated hand, in comparison to the weight of a similar filter paper in a control hand with no treatment. In addition, the effect of the toxin can be measured by visual inspection of both filter papers before and after the injection of the toxin. The treated hand shows significantly less or no moisture released after the administration of the toxin.

The foregoing detailed description of various embodiments of the invention has been presented for the purpose of illustration and description only and is not to be interpreted as limiting the scope of the invention in any way. A skilled person will realize that many modifications and variations can be made within the scope of the present invention.

What is claimed is:

1. A method of treating fibromyalgia, tension headache, hyperhydrosis, hemifacial spasm, or blepharospasm comprising administering a therapeutically effective amount of a composition comprising an injectable solution comprising Gonyautoxin 2 and Gonyautoxin 3 in a ratio of about 2:1 to a subject in need thereof, wherein said administration is via injection.

2. A method of treating fibromyalgia, tension headache, hyperhydrosis, hemifacial spasm, or blepharospasm comprising administering a therapeutically effective amount of a composition to a subject in need thereof, wherein the active ingredients of the composition consist of Gonyautoxin 2 and Gonyautoxin 3, and wherein the composition further comprises a pharmalogically acceptable carrier.

3. The method of claim 1, wherein the therapeutically effective amount of the composition includes from 1 to about 5000 units of activity of phycotoxins.

4. The method of claim 1, wherein the injection comprises not more than two milliliters of the composition.

5. The method of claim 2, wherein the composition comprises an injectable solution that is administered via injection.

6. The method of claim 2, wherein the composition comprises a topical preparation that is applied locally.

7. The method of claim 2, wherein the therapeutically effective amount of the composition includes from 1 to about 5000 units of activity of phycotoxins.

8. The method of claim 5, wherein the injection comprises not more than two milliliters of the composition.

9. The method of claim 5, wherein the injectable solution comprises Gonyautoxin 2 and Gonyautoxin 3 in a ratio of 2:1.

10. The method of claim 6, wherein the topical preparation comprises from about 0.0001% to about 0.01% by weight of Gonyautoxin 2 and Gonyautoxin 3.

* * * * *